(12) United States Patent
Ting

(10) Patent No.: US 6,561,905 B2
(45) Date of Patent: May 13, 2003

(54) SKIN-IRRITATING GAME MACHINE

(76) Inventor: Wu-Shiung Ting, No. 65, Lane 30, Lo Li Third St., An Lo Dist., Keelung (TW)

( * ) Notice: Subject to any disclaimer, the term of this patent is extended or adjusted under 35 U.S.C. 154(b) by 315 days.

(21) Appl. No.: 09/761,706

(22) Filed: Jan. 18, 2001

(65) Prior Publication Data

US 2002/0094864 A1 Jul. 18, 2002

(51) Int. Cl.[7] .................................................. A63F 13/00
(52) U.S. Cl. ............................ 463/30; 463/1; 463/9; 273/430; 273/432; 273/460; 434/327
(58) Field of Search .................. 463/30, 9, 1; 273/430, 273/432, 460; 434/322, 327, 335, 338

(56) References Cited

U.S. PATENT DOCUMENTS

| | | | | |
|---|---|---|---|---|
| 1,647,276 A | * | 11/1927 | Daman | 434/338 |
| 3,561,136 A | * | 2/1971 | Solow | 434/338 |
| 3,841,316 A | * | 10/1974 | Meyer | 273/454 |
| 3,851,875 A | * | 12/1974 | Breslow et al. | 273/460 |
| 3,869,810 A | * | 3/1975 | Ronalds | 434/338 |
| 3,886,953 A | * | 6/1975 | Pope | 131/270 |
| 4,058,116 A | * | 11/1977 | Fields | 273/460 |
| 4,358,118 A | * | 11/1982 | Plapp | 273/460 |
| 5,209,494 A | * | 5/1993 | Spector | 273/460 |
| 5,326,269 A | * | 7/1994 | Kalik et al. | 434/338 |

* cited by examiner

Primary Examiner—Jessica Harrison
(74) Attorney, Agent, or Firm—Bacon & Thomas, PLLC

(57) ABSTRACT

A skin-irritating game machine include a main unit and a plurality of control cables respectively connected to the main unit, each control cable having two metal contact elements adhered to the skin a respective player to form a respective electric loop through which a voltage is outputted from the main unit to the player who loses the game.

6 Claims, 6 Drawing Sheets

SKIN-IRRITATING GAME MACHINE

BACKGROUND OF THE INVENTION

The present invention relates to game machines and, more specifically, to a skin-irritating game machine, which outputs a voltage to irritate the skin of the player who loses the game.

Various palm-top game machines, such as electronic pet game machines, match-pair game machines, etc. have been disclosed, and have appeared on the market. These machines may have sound and lighting effect generating means to attract consumers. Further, various exercising and massaging apparatus are commercially available for use to exercise the body physically and/or to stimulate the circulation of blood.

SUMMARY OF THE INVENTION

The present invention provides a skin-irritating game machine, which can be used to play games as well as to stimulate the circulation of blood. According to the present invention, the skin-irritating game machine comprises a main unit and a plurality of control cables. The main unit comprises a control circuit assembly, a plurality of input buttons for signal input into the control circuit to set a predetermined reference value, and a plurality of electric sockets respectively connected to the control circuit assembly. The control circuit assembly comprises a battery power supply, an input circuit, an IC chip, and a skin-irritating control circuit. The control cables are respectively connected to the electric sockets of the main unit, comprising a cable, an electric plug disposed at one end of the cable and connected to one electric socket of the main unit, two metal contact elements connected in parallel to one end of the cable remote from the electric plug and adapted for adhering to the skin of a player, and a button connected between the cable and the metal contact elements. When the player presses the button of the respective control cable after a reference value had been set through the buttons of the main unit, a signal is provided to the IC chip for comparison with the set reference value, and the IC chip drives the skin-irritating control circuit to send an irritating voltage through the metal contact elements of the respective control cable to irritate the skin of the player if the value of the comparison result is beyond a predetermined range of the set reference value.

DETAILED DESCRIPTION OF THE PREFERRED EMBODIMENT

Figure 1:
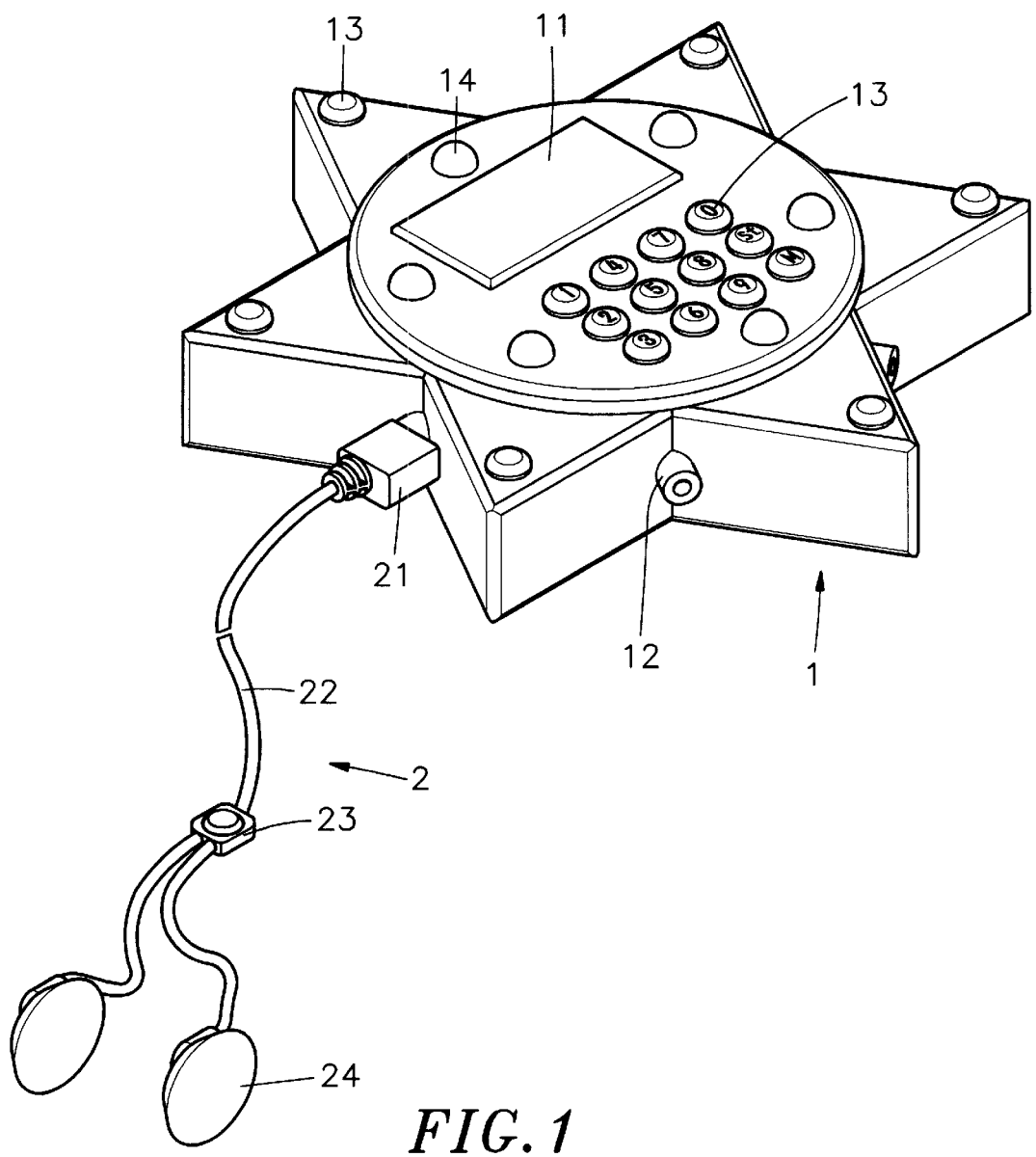
FIG. 1 is an elevational view of a skin-irritating game machine according to the present invention.
Figure 2:
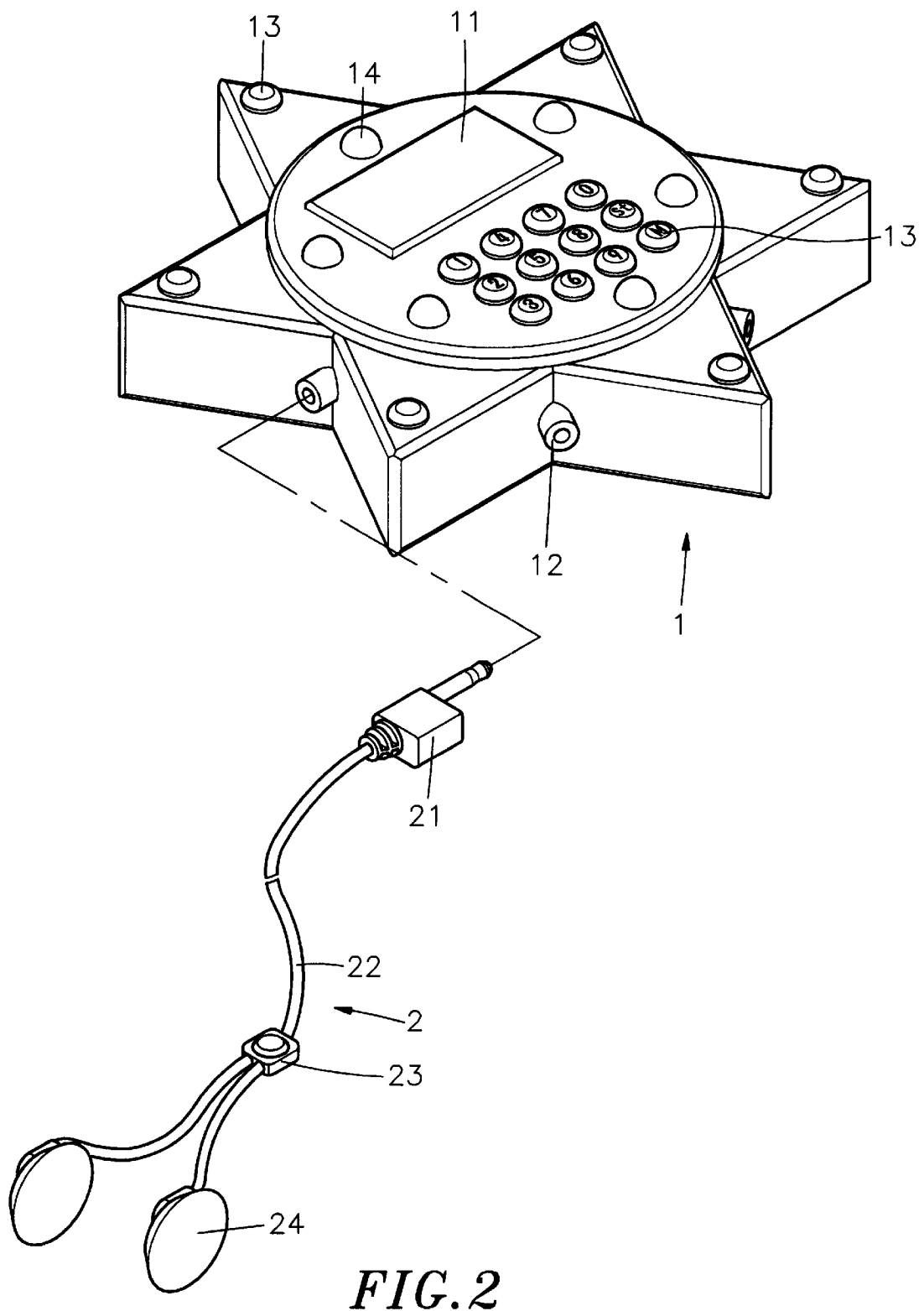
FIG. 2 is similar to FIG. 1 but showing the control cable disconnected from the main unit.
Figure 3:
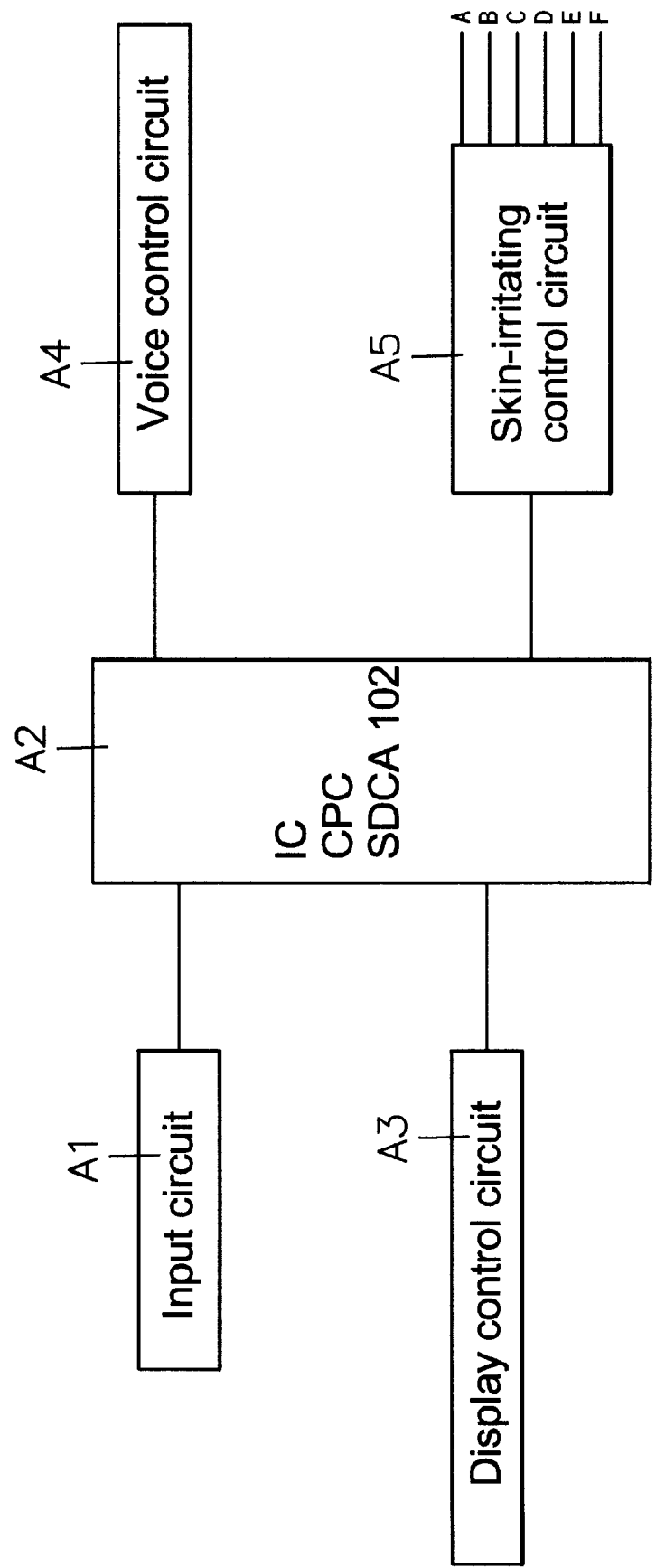
FIG. 3 is a system block diagram of the present invention.
Figure 4:
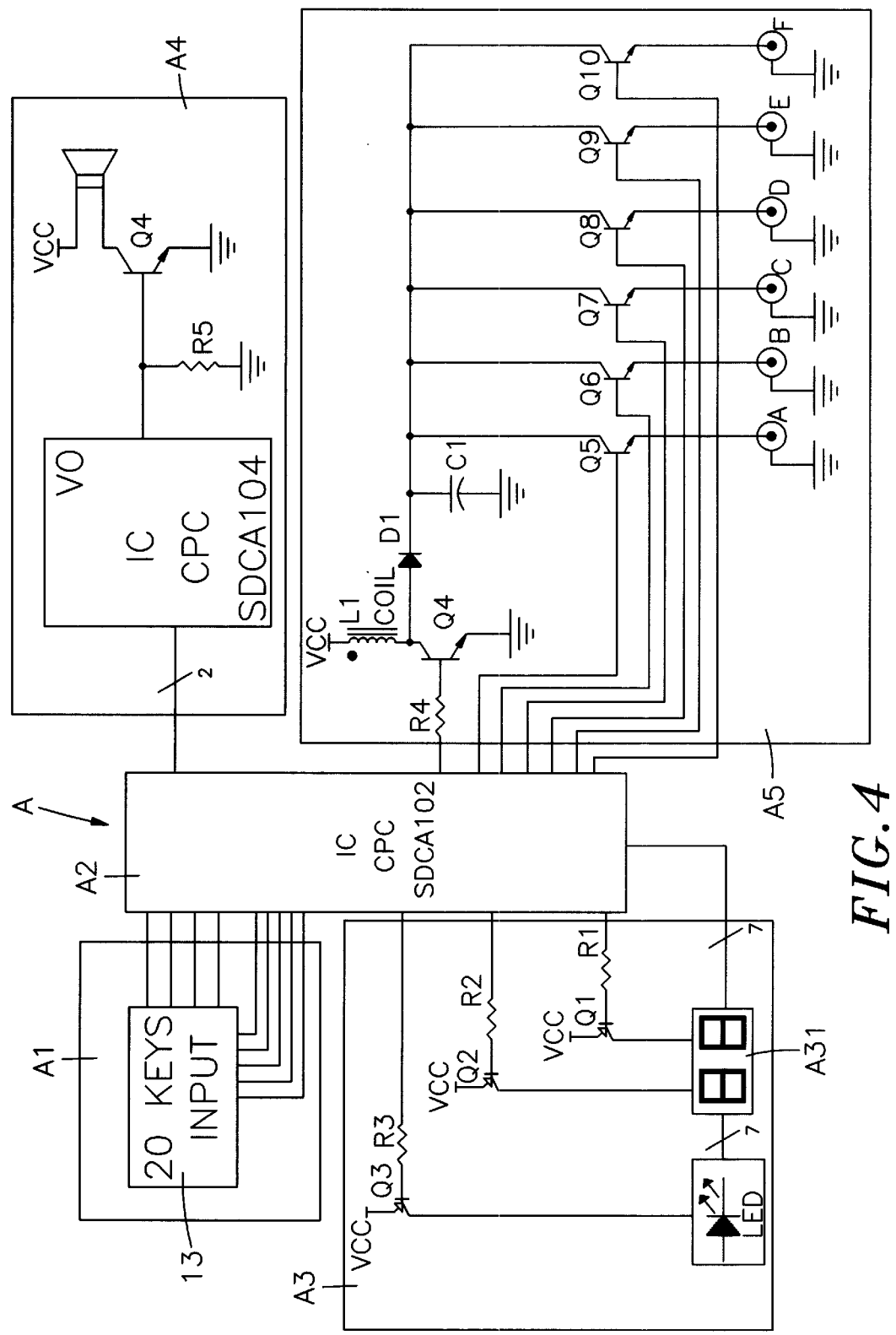
FIG. 4 is a circuit diagram of the present invention.

Referring to FIGS. 1 and 2, a skin-irritating game machine in accordance with the present invention is generally comprised of a main unit 1, and at least one control cable 2. The main unit 1 comprises a transparent glass window 11, a plurality of electric sockets 12, a set of buttons 13, and a set of indicator lights 14 respectively disposed on the outside. The main unit 1 further comprises a control circuit assembly A disposed on the inside. The control circuit assembly A comprises an input circuit A1, an IC chip (for example, IC CPC SDCA102) A2, a display control circuit A3, a voice control circuit A4, and a skin-irritating control circuit A5. A battery power source (not shown) is disposed inside the main unit 1 and connected to the input circuit A1 to provide the control circuit assembly A the necessary working voltage. The control cable 2 comprises a cable 22, an electric plug 21 disposed at one end of the cable 22 and adapted for connecting to one electric socket 12 of the main unit 1, two metal contact elements 24 connected in parallel to one end of the cable 22 remote from the electric plug 21, and a button 23 disposed between the cable 22 and the metal contact elements 24. Pressing the button 23 of the control cable 2 or either button 13 of the main unit 1 triggers the skin-irritating control circuit A5 to send an irritating voltage through the metal contact elements 24 to irritate the skin of the player.

When pressing the buttons 13 or 23 to produce a trigger signal, the trigger signal is sent to the IC chip A2 and compared with the reference value set in the IC chip A2. When matched, the skin-irritating control circuit A5 is triggered to output a skin-irritating signal to the metal contact elements 24 through the corresponding electric socket 12, the electric plug 21 and the cable 22 intermittently, forming with the operator's skin a conducting loop.

Figure 5:
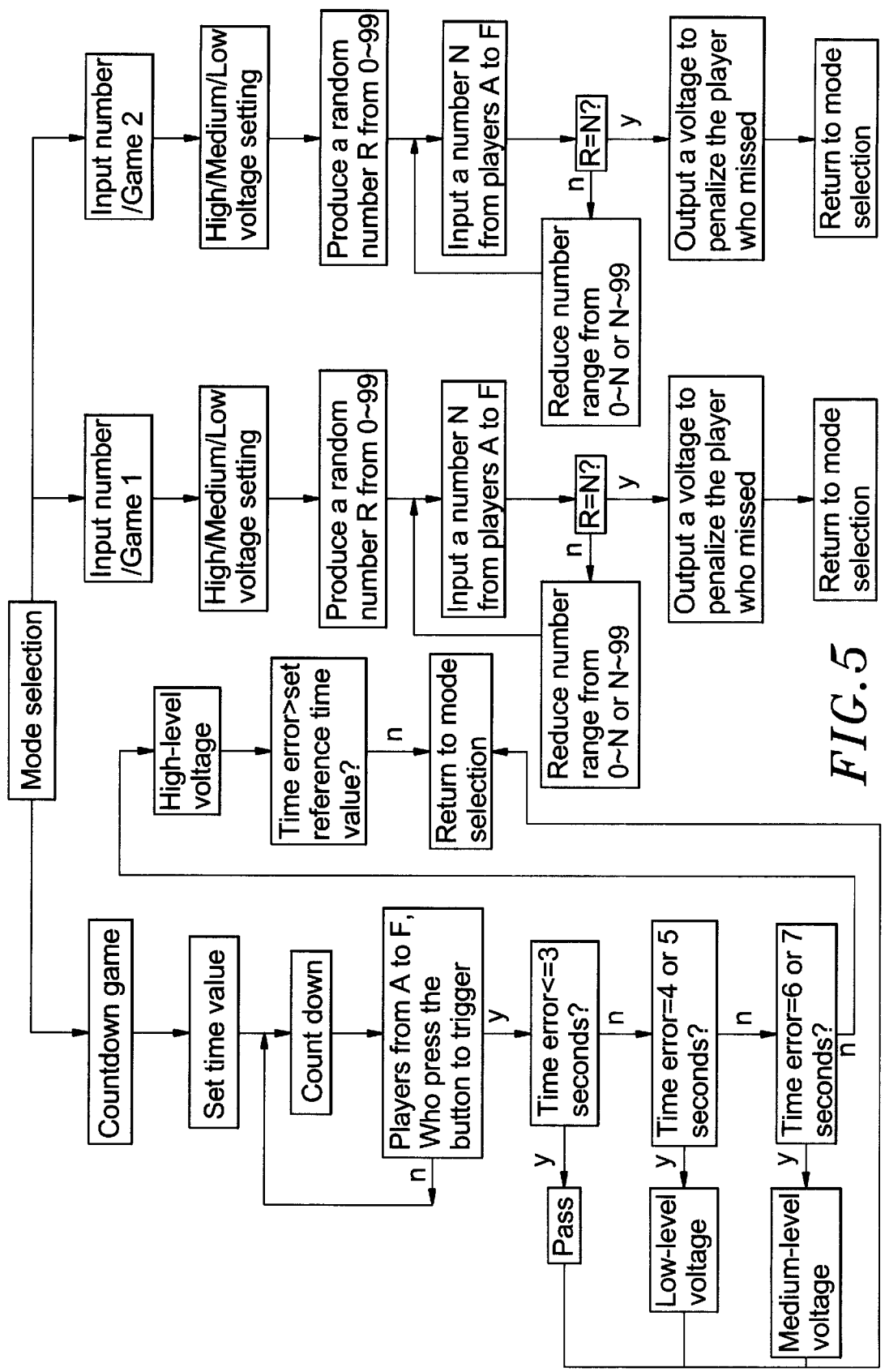
FIG. 5 is an operation flow chart of the present invention.

Referring to FIG. 5, when multiple players connect respective control cables 2 to the electric sockets 12 of the main unit 1, the metal elements 24 of the control cables 2 are respectively adhered to the skin of the respective players, and the players can than start a countdown game, or a number-guess game.

1. With respective to the countdown game, a predetermined reference time value is set through the buttons 13 of the main unit 1 before starting the game. After setting of the reference time value, every player counts the time silently inside the mind and then presses the button 23 of the respective cable 2 when thought that the time is up. Upon pressing of the button 23, a signal is inputted into the IC chip A2 for comparison with the set reference time value. If the value of the signal from the cable 2 is within a set tolerance range (the set reference time value±a predetermined range), the respective player is passable and receives no penalty. If the value of the signal from the cable is out of the set tolerance range, the respective player is penalized at a degree subject to the degree of difference from the set tolerance range, i.e., the IC chip A2 outputs a respective voltage signal to trigger the skin-irritating control circuit A5, causing it to output a voltage, at value and length of time subject to the degree of difference from the set tolerance range, through the metal contact elements 24 of the respective cable 2 to irritate the skin of the respective player.

2. With respective to the number guess game, a predetermined reference voltage value is set through the buttons 13 of the main unit 1 before starting the game. After setting of the reference voltage value, the IC chip A2 produces a random number from 1 through 13, and then the respective player inputs a number to guess the random number and then presses the button 23 of the respective cable 2 to confirm the number. After pressing of the button of the cable 2, a signal is inputted into the IC chip A2 for comparison with the set reference number. If the number inputted from the player is equal or approximately equal to the set reference number, the respective player is passable and receives no penalty. If the number inputted from the player is far from the set reference number, the respective player is penalized at a degree subject to the degree of difference from the set reference number, i.e., the IC chip A2 outputs a respective voltage signal to trigger the skin-irritating control circuit A5, causing it to output a voltage, at value and length of time subject to the degree of difference from the set reference number, through the metal contact elements 24 of the respective cable 2 to irritate the skin of the respective player.

Figure 6:
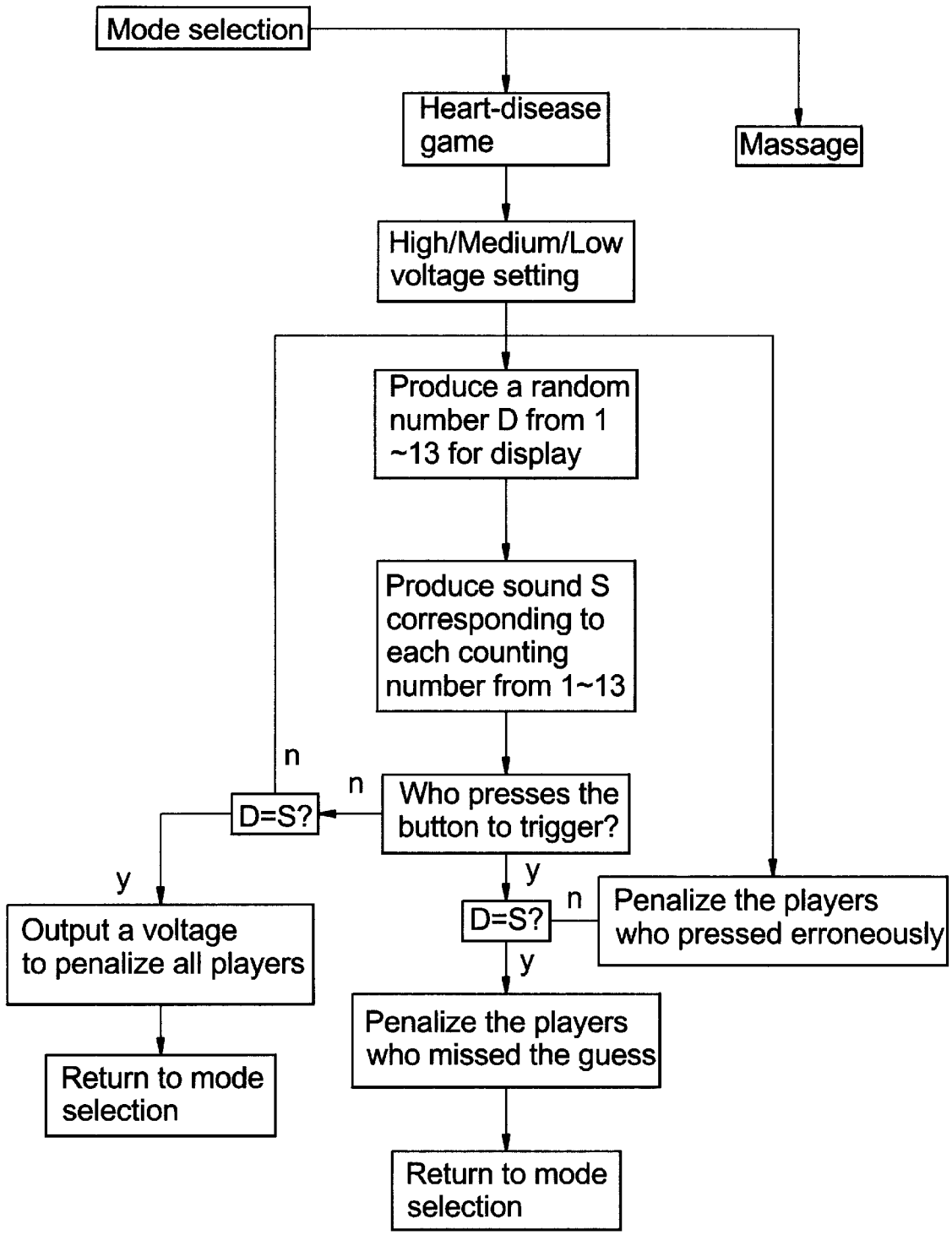
FIG. 6 is another operation flow chart of the present invention.

Referring to FIG. 6, after cables 2 have been respectively connected to the electric sockets 12 of the main unit 1, the metal contact elements 24 are respectively adhered to the skin of the players to start a heart-disease game. Before starting the heart-disease game, a predetermined reference voltage value is set through the buttons 13 of the main unit 1 before starting the game. After setting of the reference voltage value, the IC chip A2 produces a random number from 1 through 13, and then drives the a LCD A31 to display the random number and the voice control circuit A4 to read the numbers from 1 through 13 for enabling the players to guess the random number. When the displayed number on the LCD A31 and the voiced number from the voice control circuit A4 match, the players immediately press the button 23 of the respective cable 2. Upon receipt of the signal from each player (the button 23 of each control cable 2), the IC chip A2 judges the order of the triggering of the players, and then drives the skin-irritating circuit A5 to outputs a respective voltage, at value and length of time subject to the order of the respective player, through the metal contact elements 24 of the respective cable 2 to irritate the skin of the respective player.

Further, the metal contact elements 24 can be adhered to the skin of a particular part of the body, and then the user can control the button 23 of the cable 2 or the buttons 13 of the main unit 1 to drive the skin-irritating control circuit A5 to output a voltage through the metal contact elements 24, so as to stimulate circulation of blood in the part of the body.

During either of the aforesaid games, the LCD A31 of the display control circuit A3 of the control circuit A is controlled to display data, and the user can see the displayed data through the transparent glass window 11. Further, the arrangement of the voice control circuit A3 and the indicator lights 14 of the main unit 1 enable the game machine to produce a sound and lighting effect.

While only one embodiment of the present invention has been shown and described, it will be understood that various modifications and changes could be made thereunto without departing the spirit and scope of the invention disclosed.

What the invention claimed is:

1. A skin-irritating game machine comprising:

a main unit, said main unit comprising a control circuit assembly, a plurality of input buttons for signal input into said control circuit to set a predetermined reference value, a plurality of electric sockets respectively connected to said control circuit assembly, said control circuit assembly comprising a battery power supply, an input circuit, an IC chip, and a skin-irritating control circuit; and a plurality of control cables respectively connected to said electric sockets of said main unit, said control cables each comprising a cable, an electric plug disposed at one end of said cable and connected to one electric socket of said main unit, and two metal contact elements connected in parallel to one end of said cable remote from said electric plug and adapted for adhering to the skin of a player;

wherein when the player presses one button assigned from the buttons of said main unit after a reference value had been set through the buttons of said main unit, a signal is provided to said IC chip for comparison with the set reference value, and said IC chip drives said skin-irritating control circuit to send an irritating voltage through the metal contact elements of the respective control cable to irritate the skin of the player if the value of the comparison result is beyond a predetermined range of the set reference value.

2. The skin-irritating game machine of claim 1, wherein said control circuit assembly further comprises a liquid crystal display.

3. The skin-irritating game machine of claim 2, wherein said main unit comprises a transparent window glass suspended above said liquid crystal display.

4. The skin-irritating game machine of claim 1, wherein said control circuit assembly further comprises a voice control circuit for voice output upon input of an input signal from the buttons of said main unit.

5. The skin-irritating game machine of claim 1, wherein said main unit further comprises a plurality of indicator lights respectively connected to said electric sockets through said control circuit assembly.

6. The skin-irritating game machine of claim 1, wherein said control cables each further comprises a button connected between the respective cable and the respective metal contact elements for inputting a signal to said control circuit assembly to drive said skin-irritating control circuit.

\* \* \* \* \*